US00PP34194P2

(12) United States Plant Patent
Yu et al.

(10) Patent No.: US PP34,194 P2
(45) Date of Patent: May 3, 2022

(54) ***RHODODENDRON* PLANT NAMED 'SPRING MATE'**

(50) Latin Name: *Rhododendron hybrida*
Varietal Denomination: Spring Mate

(71) Applicants: SOUTH CHINA AGRICULTURAL UNIVERSITY, Guangzhou (CN); LU'AN YUGARDEN HORTICULTURE Co., Ltd., Lu'an (CN)

(72) Inventors: Shujun Yu, Guangzhou (CN); Xiaohan Yu, Lu'an (CN); Yiqi Feng, Guangzhou (CN)

(73) Assignees: South China Agricultural University, Guangzhou (CN); Lu'an Yugarden Horticulture Co., Ltd., Lu'an (CN)

( * ) Notice: Subject to any disclaimer, the term of this patent is extended or adjusted under 35 U.S.C. 154(b) by 0 days.

(21) Appl. No.: 17/507,637

(22) Filed: Oct. 21, 2021

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./226, 238
See application file for complete search history.

*Primary Examiner* — Karen M Redden
(74) *Attorney, Agent, or Firm* — C. Anne Whealy

(57) ABSTRACT

A new and distinct cultivar of *Rhododendron* plant named 'Spring Mate', characterized by its upright to broadly spreading and mounding plant habit; moderately vigorous growth habit and moderate growth rate; freely branching habit and dense and bushy appearance; dark green-colored leaves; freely flowering habit; ruffled semi-double flowers that are vivid reddish orange in color; and good garden performance and temperature tolerance.

2 Drawing Sheets

Figure 1:
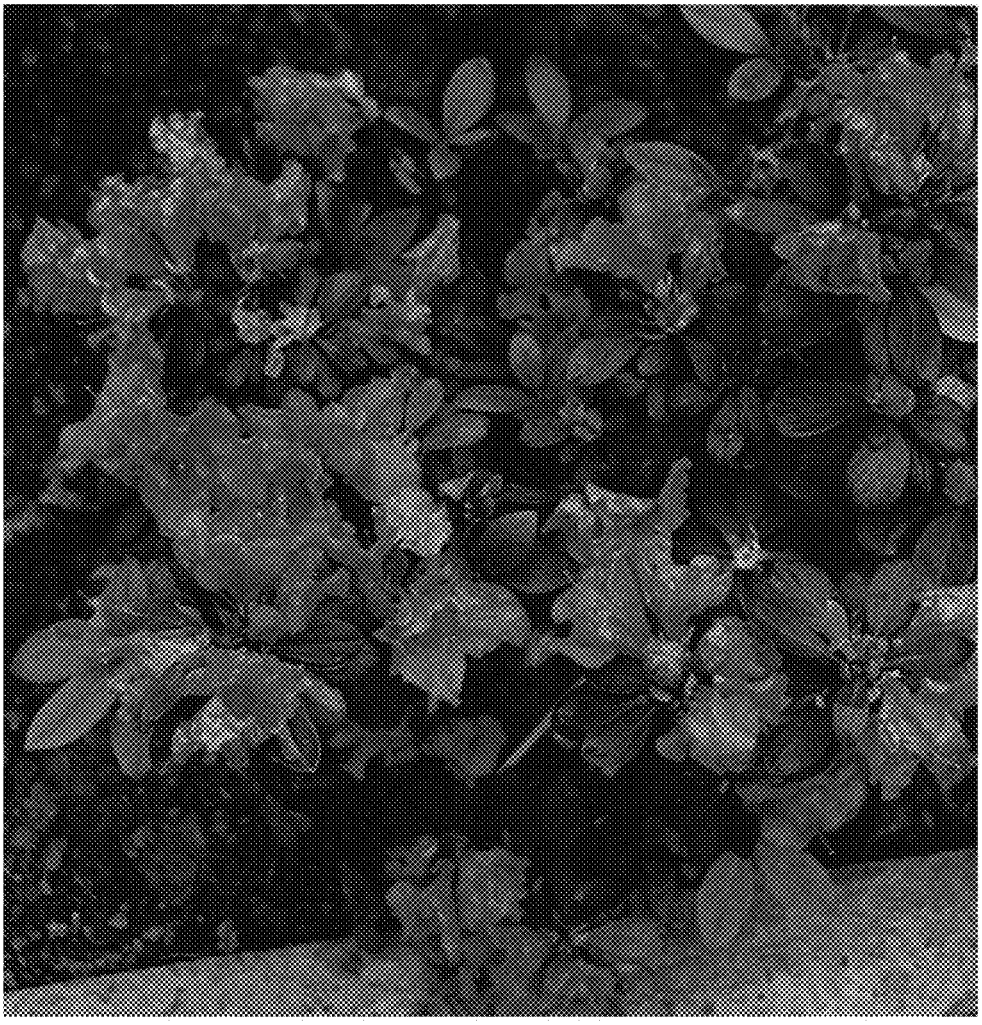

Botanical designation: *Rhododendron hybrida.*
Cultivar denomination: 'SPRING MATE'.

BACKGROUND OF THE INVENTION

The present Invention relates to a new and distinct cultivar of *Rhododendron* plant, botanically known as *Rhododendron hybrida*, commercially referred to as an evergreen *Rhododendron* plant and hereinafter referred to by the name 'Spring Mate'.

The new *Rhododendron* plant is a product of a planned breeding program conducted by the Inventors in Lu'an City, Anhui Province, China. The objective of the breeding program is to create new evergreen *Rhododendron* plants having uniform growth habit, attractive flower forms and color with good garden performance in Eastern China.

The new *Rhododendron* plant originated from a cross-pollination made by the Inventors in April, 2013 in Lu'an City, Anhui Province, China of *Rhododendron hybrida* 'Bawang Hong', not patented, as the female, or seed, parent with *Rhododendron hybrida* 'Xia Hong', not patented, as the male, or pollen, parent. The new *Rhododendron* plant was discovered and selected by the Inventors as a single flowering plant within the progeny of the stated cross-pollination in a controlled greenhouse environment in Lu'an City, Anhui Province, China in April, 2018

Asexual reproduction of the new *Rhododendron* plant by semi-hardwood stem cuttings taken in a controlled greenhouse environment in Lu'an City, Anhui Province, China since August, 2018 has shown that the unique features of this new *Rhododendron* plant are stable and reproduced true to type in successive generations.

SUMMARY OF THE INVENTION

Plants of the new *Rhododendron* have not been observed under all possible combinations of environmental conditions and cultural practices. The phenotype may vary somewhat with variations in environmental conditions such as temperature, daylength and light intensity without, however, any variance in genotype. The following traits have been repeatedly observed and are determined to be the unique characteristics of 'Spring Mate'. These characteristics in combination distinguish 'Spring Mate' as a new and distinct *Rhododendron* plant:

1. Upright to broadly spreading and mounding plant habit.
2. Moderately vigorous growth habit and moderate growth rate.
3. Freely branching habit; dense and bushy appearance.
4. Dark green-colored leaves.
5. Freely flowering habit.
6. Ruffled semi-double flowers that are vivid reddish orange in color.
7. Good garden performance and temperature tolerance.

Plants of the new *Rhododendron* differ primarily from plants of the female parent, 'Bawang Hong', in the following characteristics:

1. Plants of the new *Rhododendron* have reddish orange-colored flowers whereas plants of 'Bawang Hong' have reddish pink-colored flowers.
2. Plants of the new *Rhododendron* are more cold temperature tolerant than plants of 'Bawang Hong'.

Plants of the new *Rhododendron* differ primarily from plants of the male parent, 'Xia Hong', in the following characteristics:

1. Plants of the new *Rhododendron* have darker green-colored leaves than plants of 'Xia Hong'.
2. Plants of the new *Rhododendron* have reddish orange-colored flowers whereas plants of 'Xia Hong' have light red-colored flowers.

Plants of the new *Rhododendron* can be compared to the plants of 'Ryukyu Red', not patented. In side-by-side comparisons, plants of the new *Rhododendron* differ primarily from plants of 'Ryukyu Red' in the following characteristics:

1. Flowers of plants of the new *Rhododendron* are more cupped-shaped and not as trumpet-shaped as plants of 'Ryukyu Red'.
2. Flowers of plants of the new *Rhododendron* have spots at the center of the flower whereas flowers of plants of 'Ryukyu Red' do not have spots.

BRIEF DESCRIPTION OF THE PHOTOGRAPHS

The accompanying colored photographs illustrate the overall appearance of the new *Rhododendron* plant showing the colors as true as it is reasonably possible to obtain in colored reproductions of this type. Colors in the photographs may differ slightly from the color values cited in the detailed botanical description which accurately describe the colors of the new *Rhododendron* plant.

The photograph on the first sheet (FIG. 1) is a side perspective view of a typical flowering plant of 'Spring Mate'.

Figure 2:
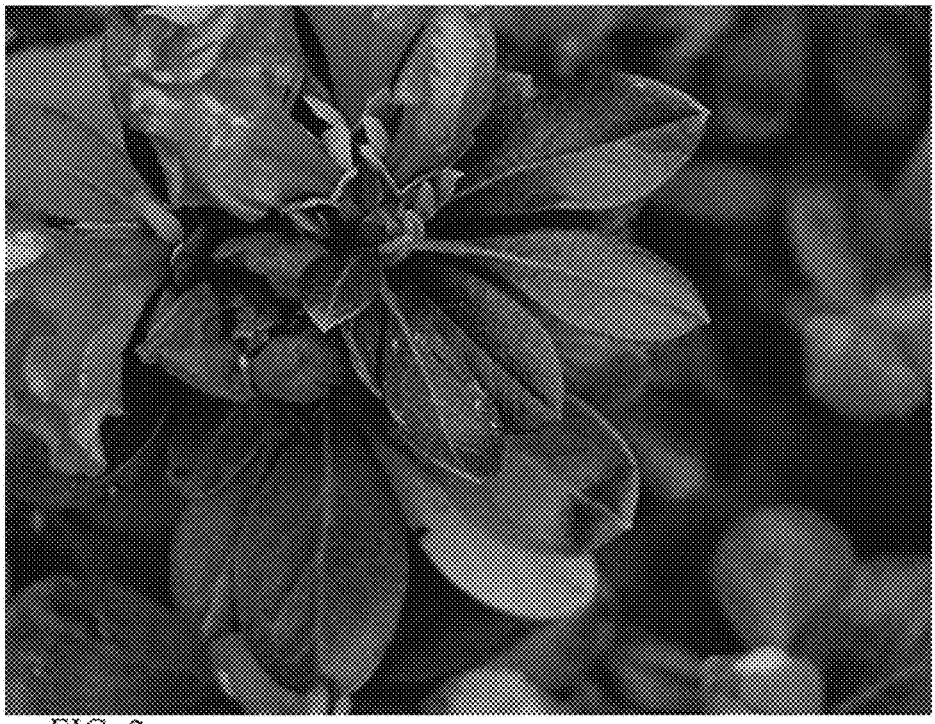

The photograph at the top of the second sheet (FIG. 2) is a close-up view of typical developing flowers of 'Spring Mate'.

Figure 3:
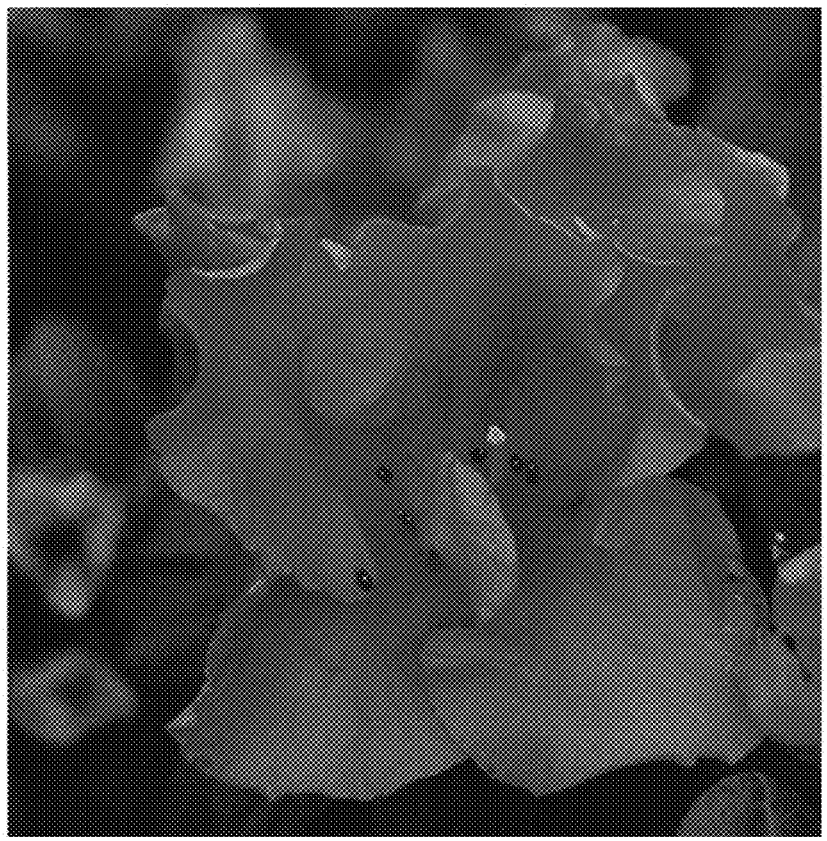

The photograph at the bottom of the second sheet (FIG. 3) is a close-up view of a typical open flower of plants of 'Spring Mate'.

DETAILED BOTANICAL DESCRIPTION

The aforementioned photographs, following observations and measurements describe plants grown during the spring in an outdoor nursery in Lu'an City, Anhui Province, China and under cultural practices typical of nursery *Rhododendron* production. During the production of the plants, day temperatures ranged from 14° C. to 22° C. and night temperatures ranged from 12° C. to 16° C. Plants used for the photographs and detailed description were five years old. In the following description, color references are made to The Royal Horticultural Society Colour Chart, 2001 Edition, except where general terms of ordinary dictionary significance are used.

Botanical classification: *Rhododendron hybrida* 'Spring Mate'.

Commercial classification: Evergreen *Rhododendron.*

Parentage:

*Female, or seed, parent.*—*Rhododendron hybrida* 'Bawang Hong', not patented.

*Male, or pollen, parent.*—*Rhododendron hybrida* 'Xia Hong', not patented.

Propagation:

*Type.*—By semi-hardwood stem cuttings.

*Time to initiate roots, summer.*—About 20 days at temperatures about 29° C.

*Time to produce a rooted young plant, summer.*—About 30 days at temperatures about 29° C.

*Root description.*—Fine, fibrous; initially white in color becoming orange brown with development; actual color of the roots is dependent on substrate composition, water quality, fertilizer type and formulation, substrate temperature and physiological age of roots.

*Rooting habit.*—Low branching; medium density.

Plant description:

*Plant form, plant and growth habit.*—Perennial and evergreen flowering subshrub; upright to broadly spreading and mounding plant habit; moderately vigorous growth habit and moderate growth rate; freely flowering habit with numerous semi-double flowers developing per plant during the flowering season.

*Branching habit.*—Freely branching habit with lateral branches potentially developing at every node; dense and bushy appearance; pinching (removal of terminal apex) will enhance lateral branch development.

*Plant height, soil level to top of foliar plane.*—About 43 cm.

*Plant height, soil level to top of floral plane.*—About 48 cm.

*Plant diameter, area of spread.*—About 48.5 cm.

*Lateral branch description.*—Length: About 15 cm. Diameter at base: About 6 mm. Internode length: About 0.9 cm to 2.2 cm. Strength: Moderately strong. Aspect: Upright to about 60° from vertical. Texture and luster: Smooth, glabrous, becoming woody with development; matte. Color: Close to 197B.

*Leaf description.*—Arrangement: Alternate; simple. Length: About 4.3 cm to 6.4 cm. Width: About 2.3 cm to 2.8 cm. Shape: Elliptic to obovate. Apex: Acute. Base: Cuneate. Margin: Entire. Venation pattern: Pinnate; reticulate. Texture and luster, upper and lower surfaces: Pubescent; matte. Color: Developing leaves, upper surface: Close to 146C. Developing leaves, lower surface: Close to 148C. Fully expanded leaves, upper surface: Close to 147A; venation, close to 147A. Fully expanded leaves, lower surface: Close to 146C; venation, close to 146C. Petioles: Length: About 2 mm to 4 mm. Diameter: About 1 mm to 2 mm. Strength: Flexible. Texture and luster, upper and lower surfaces: Smooth, glabrous; matte. Color, upper surface: Close to 146D. Color, lower surface: Close to 152C.

Flower description:

*Flower appearance and arrangement.*—Semi-double flowers arranged mostly upright to outwardly in clusters at terminals and sub-terminals.

*Natural flowering season.*—Plants of the new *Rhododendron* flower in the spring in Eastern China.

*Flowering habit.*—Freely flowering habit with usually about three to seven flowers per terminal or sub-terminal; during the flowering season, about 40 to 120 open flowers develop per plant.

*Flower longevity.*—Flowers are durable and long-lasting; depending on the temperature, flowers last about five days on the plant, dependent on ambient temperatures; flowers not persistent.

*Fragrance.*—If present, slightly fragrant.

*Flower diameter.*—About 6.6 cm to 7.4 cm.

*Flower depth.*—About 5.6 cm to 5.8 cm.

*Flower buds.*—Length: About 4.3 cm to 4.6 cm. Diameter: About 1.6 cm to 1.9 cm. Shape: Elliptic. Texture and luster: Smooth, glabrous; matte. Color: Close to 34A.

*Petals.*—Quantity and arrangement: About six to eight petals arranged in about two or three whorls and fused at the base. Length: About 5 cm to 5.3 cm. Width: About 3 cm to 3.5 cm. Shape: Broadly obovate. Apex: Obtuse; undulate, ruffled. Margin: Entire; undulate; ruffled. Texture, upper and lower surfaces: Smooth, glabrous; matte. Color: When opening and fully opened, upper surface: Close to 34A; central spots and speckles, close to 53A. When opening and fully opened, lower surface: Close to 34A.

*Sepals.*—Arrangement: Five in a single whorl, fused at the base forming a campanulate calyx. Length: About 1.3 cm to 1.5 cm. Width: About 8 mm to 9 mm. Shape: Broadly elliptic. Apex: Acute. Base: Fused. Margin: Entire. Texture and luster, upper and lower surfaces: Smooth, glabrous; matte. Color, upper and lower surfaces: Close to 135D.

*Peduncles.*—Length: About 1.2 cm to 1.7 cm. Diameter: About 2 mm to 3 mm. Angle: Upright to outwardly. Strength: Flexible. Texture and luster: Smooth, glabrous; matte. Color: Close to 135D.

*Reproductive organs.*—Androecium: Quantity of stamens per flower: About six to nine. Filament length: About 2.7 cm to 3.5 cm. Filament color: Close to 38A. Anther shape: Narrowly elliptic. Anther length: About 2 mm to 3 mm. Anther width: About 1 mm to 2 mm. Anther color: Close to N34A. Pollen amount: Abundant. Pollen color: Close to 155D. Gynoecium: Pistil length: About 4 cm to 4.2 cm. Stigma shape: Broadly elliptic. Stigma diameter: About 1 mm to 2 mm. Stigma color: Close to 37C. Style length: About 3.9 cm to 4.1 cm. Style color: Close to 38A. Ovary color: Close to 134A.

*Fruits and seeds.*—To date, fruit and seed development have not been observed on plants of the new *Rhododendron.*

Garden performance & temperature tolerance: Plants of the new *Rhododendron* have been observed to be very tolerant to rain, wind and temperatures ranging from about −8° C. to about 38° C.

Pathogen & pest resistance: To date, plants have not been observed to be resistant to pathogens and pests common to *Rhododendron* plants.

It is claimed:

1. A new and distinct cultivar of *Rhododendron* plant named 'Spring Mate' as illustrated and described.

* * * * *